United States Patent
Sakagawa et al.

(10) Patent No.: US 9,113,779 B2
(45) Date of Patent: Aug. 25, 2015

(54) IMAGE PROCESSING APPARATUS, IMAGE PROCESSING METHOD, AND PROGRAM RECORDING MEDIUM

(75) Inventors: Yukio Sakagawa, Tokyo (JP); Yasufumi Takama, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 752 days.

(21) Appl. No.: 13/217,725

(22) Filed: Aug. 25, 2011

(65) Prior Publication Data

US 2012/0050282 A1 Mar. 1, 2012

(30) Foreign Application Priority Data

Aug. 30, 2010 (JP) ................................ 2010-192386

(51) Int. Cl.
*A61B 3/00* (2006.01)

(52) U.S. Cl.
CPC ........... *A61B 3/0025* (2013.01); *G06T 2210/41* (2013.01)

(58) Field of Classification Search
None
See application file for complete search history.

(56) References Cited

U.S. PATENT DOCUMENTS

| | | | | |
|---|---|---|---|---|
| 5,989,189 A | * | 11/1999 | LeBlanc et al. | 600/437 |
| 2006/0077349 A1 | | 4/2006 | Kushida | |
| 2006/0229513 A1 | | 10/2006 | Wakai | |
| 2008/0084538 A1 | * | 4/2008 | Maeda et al. | 351/206 |
| 2009/0310846 A1 | * | 12/2009 | Lemchen | 382/132 |
| 2010/0092091 A1 | * | 4/2010 | Kanda | 382/190 |
| 2010/0202677 A1 | | 8/2010 | Imamura | |
| 2012/0120368 A1 | * | 5/2012 | Fujimora et al. | 351/206 |

FOREIGN PATENT DOCUMENTS

| | | |
|---|---|---|
| CN | 101268928 A | 9/2008 |
| CN | 101563017 A | 10/2009 |
| CN | 101751680 A | 6/2010 |
| EP | 1872713 A1 | 1/2008 |
| EP | 2030570 A2 | 3/2009 |
| JP | 2006-102097 A | 4/2006 |
| JP | 2007-289347 A | 11/2007 |
| JP | 2007289347 A * | 11/2007 |
| JP | 2008-073099 A | 4/2008 |
| JP | 2009-061203 A | 3/2009 |
| JP | 2010-094381 A | 4/2010 |
| JP | 2010-142498 A | 7/2010 |
| WO | 2010/071091 A | 6/2010 |

OTHER PUBLICATIONS

Drexler, et al., "State-of-the-art retinal optical coherence tomography", Progress in Retinal and Eye Research, (2008), pp. 45-88, vol. 27.

* cited by examiner

*Primary Examiner* — Xiao Wu
*Assistant Examiner* — Steven Elbinger
(74) *Attorney, Agent, or Firm* — Canon U.S.A., Inc. IP Division

(57) ABSTRACT

An image processing apparatus includes an analysis unit configured to obtain information regarding an order of display of a plurality of layers from a cross-sectional image, and a display control unit configured to perform control such that methods for displaying the plurality of layers are sequentially changed and the plurality of layers are displayed on a display unit on the basis of the information regarding the order of display.

13 Claims, 8 Drawing Sheets

FIG. 7A
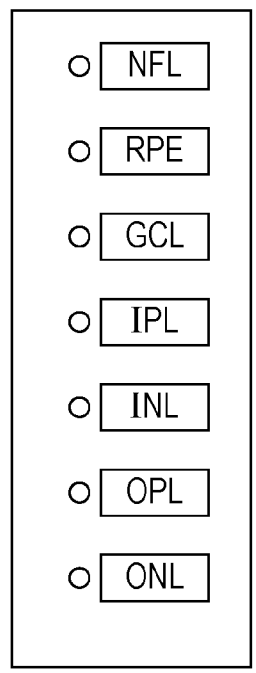
FIG. 7B
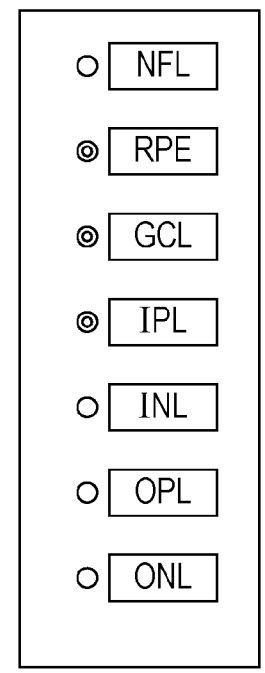
FIG. 7C
| LAYER NAME | ORDER | IMPORTANCE |
|---|---|---|
| ○ NFL | 1 | 10 |
| ◉ RPE | 2 | 9 |
| ◉ GCL | 3 | 8 |
| ◉ IPL | 4 | 8 |
| ○ INL | 5 | 7 |
| ○ OPL | 6 | 6 |
| ○ ONL | 7 | 5 |

IMAGE PROCESSING APPARATUS, IMAGE PROCESSING METHOD, AND PROGRAM RECORDING MEDIUM

BACKGROUND OF THE INVENTION

1. Field of the Invention

The present invention relates to a technique for displaying layers extracted from a cross-sectional image of an object.

2. Description of the Related Art

The technique of optical coherence tomography (OCT) is adopted in the medical field. For example, a cross-sectional image pickup apparatus for eyes enables observation of the state of the inside of layers of a retina in a three-dimensional manner. The cross-sectional image pickup apparatus is attracting attention in these years because the cross-sectional image pickup apparatus is useful to properly diagnose diseases.

In the related art of analysis of the layers of a retina, boundaries between the layers of a retina are determined using various methods. In Japanese Patent Laid-Open No. 2008-073099, a technique is disclosed in which the positions of boundaries between layers are obtained by sequentially referring to the values of pixels of a cross-sectional image in a depth direction. In order for an ophthalmologist to make a diagnosis, it is necessary to recognize each layer included in a retina, and the shape and the thickness of each layer are displayed or each layer is displayed in a three-dimensional manner in a cross-sectional image of the retina. However, if an operator selects, in order to observe the state of each layer after the boundaries between layers of a retina are determined, a layer to be observed from among multiple layers and performs an operation for switching the display, there is a problem in that the operation is complex.

SUMMARY OF THE INVENTION

The present invention makes an operation for observing a cross-sectional image efficient and easy.

That is, an image processing apparatus according to an aspect of the present invention includes an analysis unit configured to obtain information regarding an order of display of a plurality of layers from a cross-sectional image, and a display control unit configured to perform control such that methods for displaying the plurality of layers are sequentially changed and the plurality of layers are displayed on a display unit on the basis of the information regarding the order of display.

Further features of the present invention will become apparent from the following description of exemplary embodiments with reference to the attached drawings.

BRIEF DESCRIPTION OF THE DRAWINGS

The accompanying drawings, which are incorporated into and constitute a part of the specification, illustrate embodiments of the invention and, together with the description, serve to explain the principles of the invention.

FIGS. 7A, 7B, and 7C are examples of display of the names of layers selected by a display apparatus 30 of the image processing apparatus 11.

DESCRIPTION OF THE EMBODIMENTS

Preferred embodiments of the present invention will be described in detail in accordance with the accompanying drawings.

First Embodiment

A first embodiment of the present invention will be described hereinafter with reference to the drawings. It is to be noted that an ophthalmologic apparatus according to this embodiment adopts an example of a display method in which layers extracted from a cross-sectional image of a retina are automatically displayed in a predetermined order.

Figure 1:
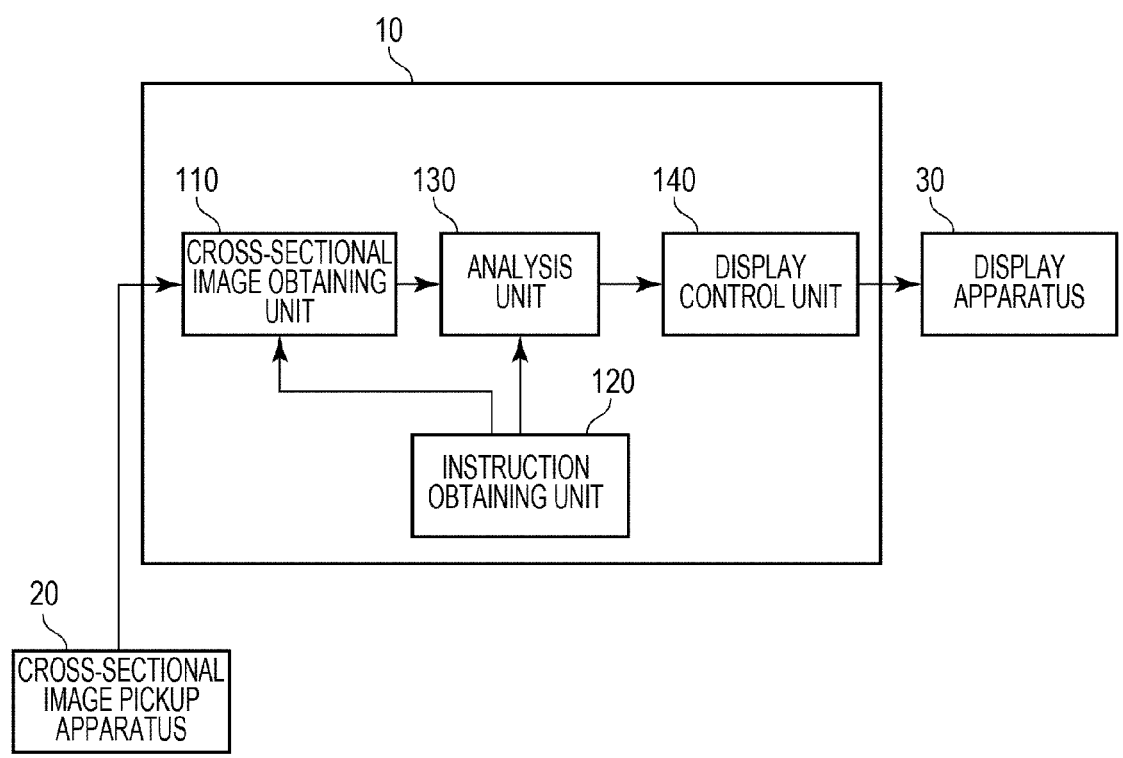
FIG. 1 is a diagram illustrating a basic configuration of an image processing apparatus 10 according to a first embodiment of the present invention.

FIG. 1 is a block diagram illustrating the entirety of an image processing system. The image processing system illustrated in FIG. 1 is configured by including an image processing apparatus 10, a cross-sectional image pickup apparatus 20, and a display apparatus 30.

The image processing apparatus 10 obtains a cross-sectional image and an image of an ocular fundus from the cross-sectional image pickup apparatus 20 or a database, which is not illustrated, and extracts layers from the cross-sectional image, in order to perform display control of the layers.

The cross-sectional image pickup apparatus 20 captures a cross-sectional image of a retina and an image of an ocular fundus by scanning the retina of an eye to be examined using measurement light. The cross-sectional image pickup apparatus 20 adopts, for example, time-domain OCT or Fourier-domain OCT. It is to be noted that since the cross-sectional image pickup apparatus 20 is a known apparatus, detailed description thereof is omitted.

The display apparatus 30 displays a cross-sectional image of an eye to be examined, layers extracted from the cross-sectional image, and the like.

First, the image processing apparatus 10 will be described in detail.

The image processing apparatus 10 is configured by including a cross-sectional image obtaining unit 110, an instruction obtaining unit 120, an analysis unit 130, and a display control unit 140.

The cross-sectional image obtaining unit 110 transmits a capture instruction to the cross-sectional image pickup apparatus 20 and obtains a captured cross-sectional image. Otherwise, the cross-sectional image obtaining unit 110 obtains a cross-sectional image from a data server, which is not illustrated, that holds cross-sectional images captured in advance.

The instruction obtaining unit 120 obtains an instruction regarding processing of an obtained cross-sectional image from an operator, who is not illustrated.

The analysis unit 130 analyzes a cross-sectional image and extracts information regarding layers from the cross-sectional image on the basis of an instruction obtained by the instruction obtaining unit 120.

The display control unit 140 processes extracted layers to convert the extracted layers into information that can be displayed. Furthermore, the display control unit 140 transmits the information to the display apparatus 30 and performs control such that the information regarding layers is sequentially displayed on the display apparatus 30 using certain display methods.

Figure 2:
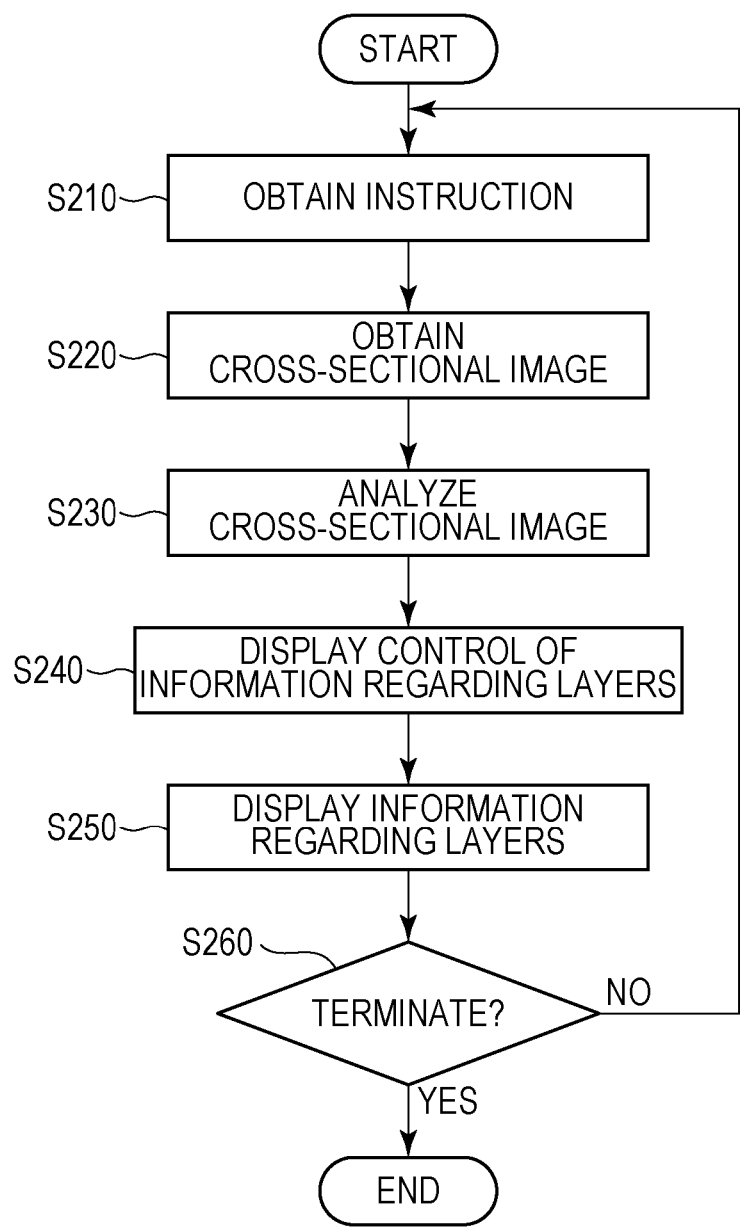
FIG. 2 is a flowchart illustrating a procedure of processing executed by the image processing apparatus 10 according to the first embodiment.

Next, s specific procedure of processing executed by the image processing apparatus 10 according to this embodiment will be described with reference to a flowchart of FIG. 2.

Step S210

In step S210, the instruction obtaining unit 120 obtains instructions input by the operator, who is not illustrated, such as specification of a cross-sectional image to be displayed. These instructions are input by the operator who uses a keyboard and a mouse, which are not illustrated, attached to the image processing apparatus 10. The obtained instructions are transmitted to the cross-sectional image obtaining unit 110 and the analysis unit 130.

Step S220

In step S220, the cross-sectional image obtaining unit 110 obtains a cross-sectional image from the cross-sectional image pickup apparatus 20. The obtained cross-sectional image is transferred to the analysis unit 130.

Step S230

In step S230, the analysis unit 130 analyzes the cross-sectional image obtained in step S220 and extracts information regarding layers. In this embodiment, the degree of importance of each extracted layer is set at the same time as the layers of a retina are extracted.

Figure 3:
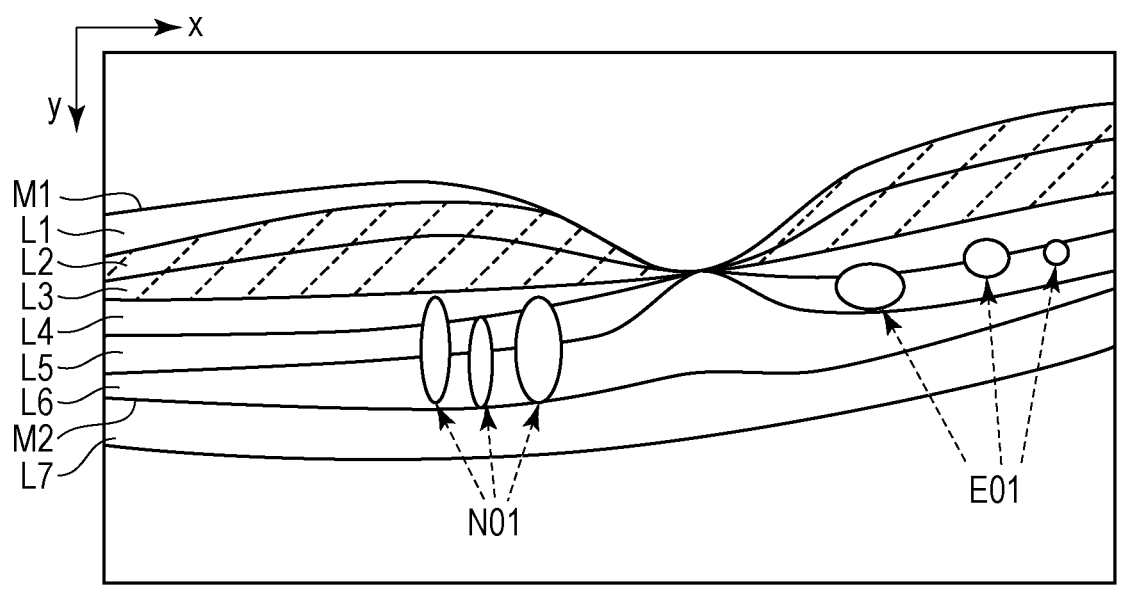
FIG. 3 is a schematic diagram of a cross-sectional image of a macula lutea of a retina.

FIG. 3 is a schematic diagram illustrating a cross-sectional image of a retina. In FIG. 3, a nerve fiber layer (NFL) L1, a ganglion cell layer (GCL) L2, an inner plexiform layer (IPL) L3, an inner nuclear layer (INL) L4, an outer plexiform layer (OPL) L5, an outer nuclear layer (ONL) L6, and a retinal pigment epithelium (RPE) L7 are illustrated. In addition, an internal limiting membrane (ILM) M1 and a photoreceptor inner segment/outer segment junction (IS/OS) M2 are illustrated. As methods for extracting layers or membranes from a cross-sectional image of a retina, multiple methods such as that disclosed in Japanese Patent Laid-Open No. 2008-073099 are known. Because pixels of a cross-sectional image of a retina have different luminance distribution between the layers, in this embodiment, the layers are extracted in accordance with the luminance distribution. It is to be noted that since different layers have texture patterns whose characteristics are different, the layers can be extracted more accurately using this information. Furthermore, the order of the layers may be used as prior information. In addition to these methods, other methods for extracting layers from a cross-sectional image may be used.

Next, the analysis unit 130 calculates the degree of importance of each layer. In this embodiment, the degree of importance of each layer is supposed to be determined in advance. Table 1 illustrates an example of the predetermined degree importance of each layer. The higher the value of importance, the more important the layer.

TABLE 1

Example of layers of retina and values of importance

| Layers of retina | Values of importance |
|---|---|
| NFL | 10 |
| GCL | 8 |
| IPL | 8 |
| INL | 7 |
| OPL | 6 |
| ONL | 5 |
| RPE | 9 |

It is to be noted that the degree of importance of each layer may be determined on the basis of an analysis of a cross-sectional image of a retina or related information that has been input, instead. For example, if white spots E01 illustrated in FIG. 3 that are characterized by high luminance thereof are detected as a result of an analysis of a cross-sectional image of a retina, the value of importance of the OPL L5, in which the white spots E01 have been detected, is determined to be 10 and the values of importance of the other layers are determined to be smaller. Similarly, if cysts N01 illustrated in FIG. 3 are detected, the values of importance of the OPL L5 and the ONL L6, in which the cysts N01 have been detected, are determined to be 10 and the values of importance of the other layers are determined to be smaller. In addition, if glaucoma is diagnosed, the values of importance of the NFL L1, the GCL L2, and the IPL L3 are determined to be 10 and the values of importance of the other layers are determined to be smaller. It is to be understood a method for determining the degrees of importance is not limited to these methods, and the values of importance of the layers of a retina may be determined using other methods.

Information regarding the extracted layers and the degrees of importance as the order of display is transferred from the analysis unit 130 to the display control unit 140 as information regarding the order of display of the layers.

Step S240

In step S240, the display control unit 140 selects a layer and performs display control of the layer on the basis of the information extracted in step S230.

In a next example according to this embodiment, as a method for selecting layers to be displayed, the analysis unit 130 selects the layers in the order of the anatomical structure of a retina, that is, in the order from the NFL L1 to the RPE L7, as illustrated in Table 1. Furthermore, if the analysis unit 130 fails to extract the layers selected in step S230, that is, for example, if the analysis unit 130 fails to extract a boundary line between the GCL L2 and the IPL L3 because of insufficient contrast between the GCL L2 and the IPL L3, the boundary line between these layers is not drawn and an alarm message is displayed. It is to be understood that display control after failure of detecting a layer is not limited to this. For example, if a boundary line between layers adjacent to each other (for example, the GCL L2 and the IPL L3) cannot be extracted, the analysis unit 130 transmits information to the display control unit 140 regarding the layers as a single layer, and accordingly the display apparatus 30 displays the layers as a single layer.

Next, the display control unit 140 performs emphasized display control in which boundary lines between selected layers are emphasized in a two-dimensional cross-sectional image. It is to be noted that the characteristics of boundary lines to be drawn, such as colors, thicknesses, and dotted, broken, or solid lines, may be changed. Furthermore, not only emphasized display of boundary lines between the layers, but also special drawing in which the color, the texture, or the like of the entire region of a selected layer is different from those of the other layers may be performed in order to distinguish the selected layer from the other layers.

It is to be noted that the method for displaying layers is not limited to two-dimensional display. If a cross-sectional image of a retina has been captured in a three-dimensional manner, display control of the cross-sectional image can accordingly be performed in a three-dimensional manner. For example, in step S230, results of extraction of three-dimensional regions of layers may be used to perform volume rendering on a selected layer using a method such as ray casting, or meshes may be created from information regarding boundary surfaces between layers and surface rendering may be performed.

Furthermore, in step S240, the display control unit 140 also controls the display time of a selected layer. In this embodiment, the display time is controlled using the degrees of importance illustrated in Table 1. Here, the display time is proportional to each degree of importance and determined using the following expression:

Display time(s)=Degree of importance×10      Expression 1

The method for determining the display time is not limited to this. For example, the following expression may be used:

Display time(s)=Degree of importance×Degree of importance×2      Expression 2

Otherwise, other determination methods such as one in which the display time is determined to be constant regardless of the degrees of importance may be used.

Although display control of each layer of a retina has been described in this embodiment, display control of each membrane of a retina such as the ILM M1 and the IS/OS M2 may be performed in the same manner.

Step S250

In step S250, the display control unit 140 sequentially displays a cross-sectional image on the display apparatus 30 using certain display methods on the basis of the information regarding the order of display of a plurality of layers obtained by the analysis unit 130.

Figure 4A:
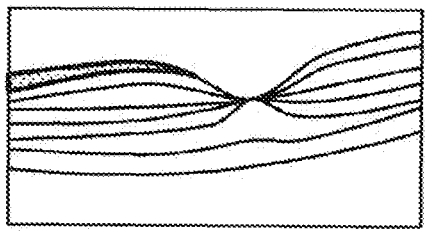
FIGS. 4A, 4B, 4C, 4D, 4E, and 4F are examples of display of a display apparatus 30 of the image processing apparatus 10.
Figure 4B:
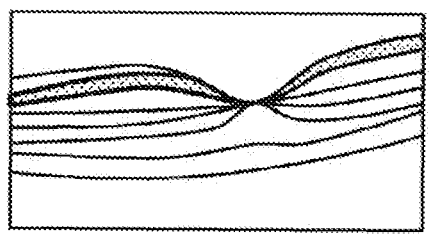
Figure 4C:
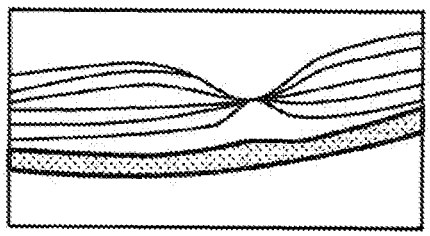
Figure 4D:
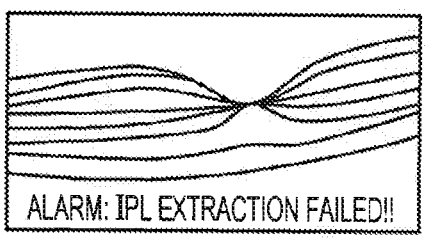
Figure 4E:
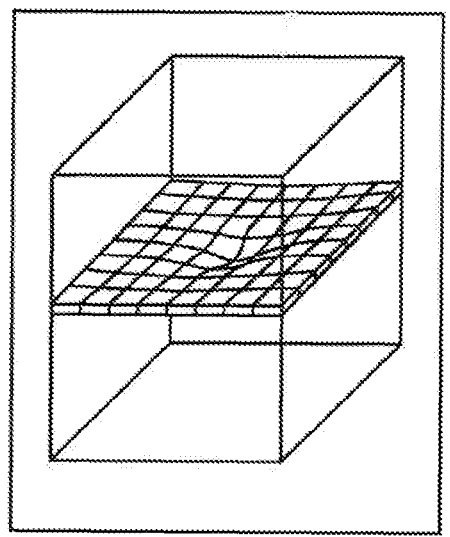
Figure 4F:
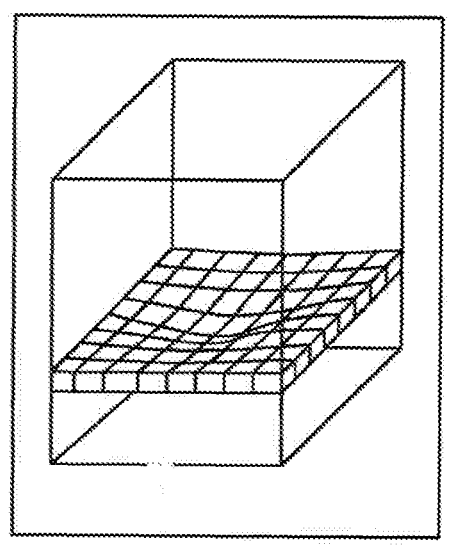

FIGS. 4A, 4B, 4C, 4D, 4E, and 4F illustrate examples of results in step S240. FIGS. 4A, 4B, 4C, and 4D illustrate examples of display of a selected layer of a two-dimensional (2D) cross-sectional image. FIGS. 4E and 4F illustrate examples of display of a selected layer of a three-dimensional (3D) cross-sectional image. Furthermore, FIGS. 4A, 4B, 4C, and 4D illustrate examples in which emphasized display of a selected layer is performed while the entirety of a retina is displayed. FIGS. 4E and 4F illustrate examples in which only a selected layer is displayed.

Step S260

In step S260, the display control unit 140 determines whether or not to terminate the processing in accordance with an instruction obtained by the instruction obtaining unit 120. The processing proceeds to step S210 if there is an instruction for displaying a next cross-sectional image. If there is no new instruction, the processing ends.

In the above-described embodiment, a cross-sectional image is analyzed and layers included in a retina are extracted, and then the layers are automatically selected and sequentially displayed using different display methods. In addition, by sequentially changing the display method on the basis of the degree of importance of each layer, the efficiency of diagnosis can be increased. In addition, by controlling the display time, the operator can efficiently and easily recognize the states of the layers with a small number of operations.

Second Embodiment

In the first embodiment, an example in which layers extracted through an analysis of a cross-sectional image of a retina are sequentially displayed using different display methods has been described. In this embodiment, a method in which the analysis unit 130 determines the order of layers to be selected on the basis of the states of the layers of a retina obtained through an analysis of a cross-sectional image.

Figure 5:
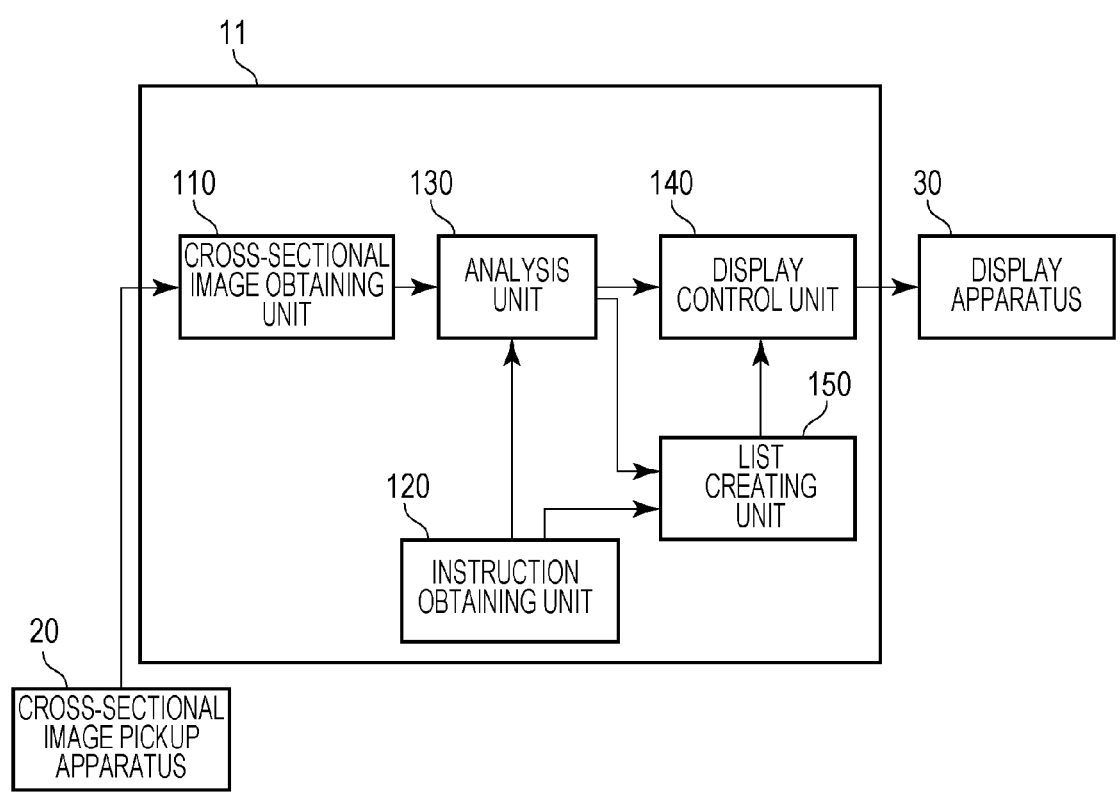
FIG. 5 is a diagram illustrating the configuration of an image processing apparatus 11 according to a second embodiment.

FIG. 5 is a diagram illustrating a functional configuration of an image processing apparatus 11 according to this embodiment. Components other than a list creating unit 150 illustrated in FIG. 5 are the same as those in the first embodiment, and therefore description thereof is omitted.

The list creating unit 150 creates a list of layers from layers extracted from a cross-sectional image by the analysis unit 130. The display control unit 140 then selects layers to be displayed and performs display control on the basis of the list of layers created by the list creating unit 150.

Figure 6:
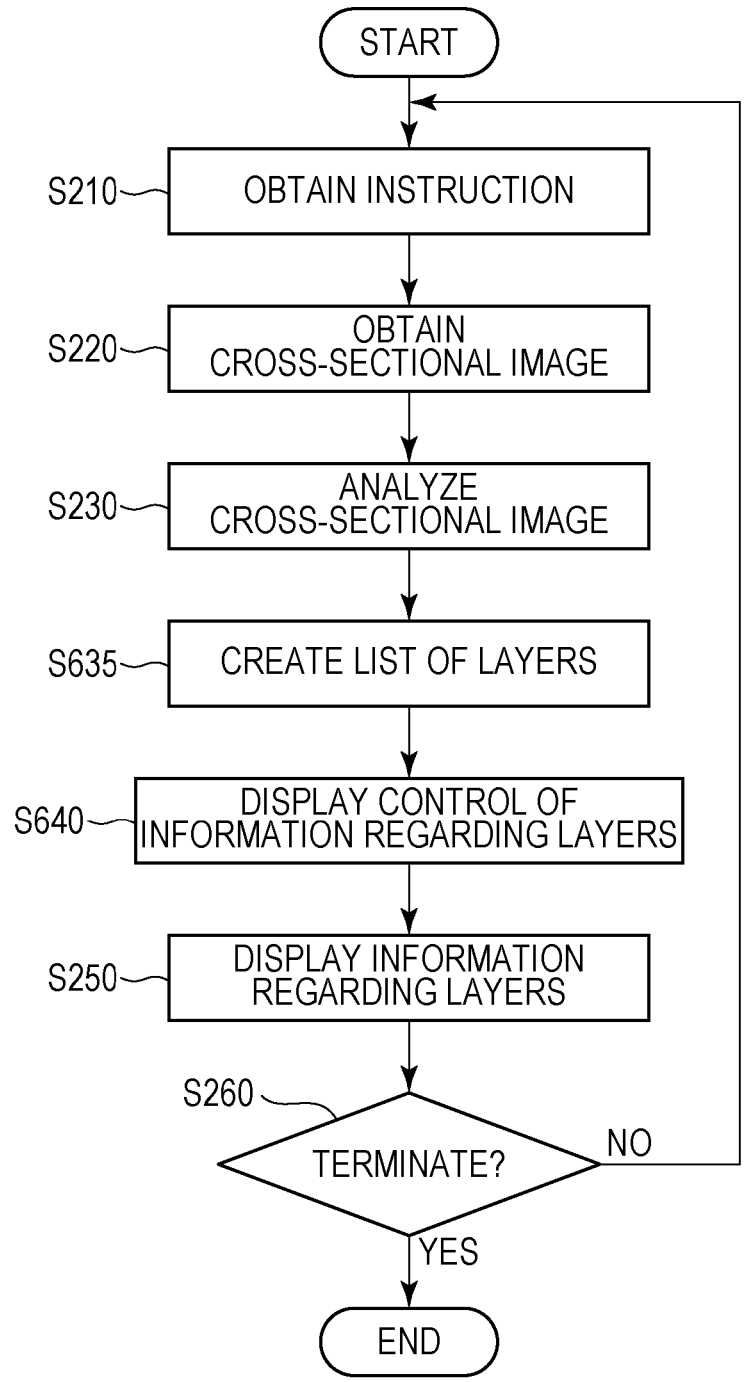
FIG. 6 is a flowchart illustrating a procedure of processing executed by the image processing apparatus 11 according to the second embodiment.

Next, a specific procedure of processing executed by the image processing apparatus 11 according to this embodiment will be described with reference to a flowchart of FIG. 6. It is to be noted that steps other than step S635 and step S640 are the same as those in the first embodiment, and therefore description thereof is omitted.

Step S635

In step S635, the list creating unit 150 creates a list of layers extracted from a cross-sectional layer by the analysis unit 130. First, for example, the list of layers is created sequentially from a layer closer to a vitreous body on the basis of the distances from the vitreous body in the anatomical structure. At this time, layers that have not been extracted are deleted from the list. Next, the list is edited to rearrange the order of the layers. Here, the order of the layers is rearranged in the order of the degree of importance of each layer calculated in step S230 by the analysis unit 130. At this time, the most importance layer comes at the top of the list. Layers of the same degree of importance are arranged in the order of the anatomical structure. Table 2 illustrates an example of the list of layers. Table 2 is a list of layers created on the basis of the degrees of importance determined in step S230 in the first embodiment. The list of layers also has information regarding the states of the layers. Here, all the layers are not selected in the initial state. It is to be understood that the initial state is not limited to this, and all the layers may be selected or randomly selected.

TABLE 2

Example of list of layers

| Order of display | Layers of retina | Values of importance | States |
|---|---|---|---|
| 1 | NFL | 10 | Not selected |
| 2 | RPE | 9 | Not selected |
| 3 | GCL | 8 | Not selected |
| 4 | IPL | 8 | Not selected |
| 5 | INL | 7 | Not selected |
| 6 | OPL | 6 | Not selected |
| 7 | ONL | 5 | Not selected |

It is to be understood that the method for creating a list of layers is not limited to this. For example, a list may be created in an order in which layers have been extracted in step S230.

Step S640

In step S640, the display control unit 140 performs display control of the layers on the basis of the list of layers created by the list creating unit 150, that is, on the basis of the information regarding the order of display of a plurality of layers. In this embodiment, the order of display is the same as the order of the list of layers.

The display time of each layer is determined in the same manner as in step S240.

According to the above-described configuration, by selecting and displaying layers sequentially from a layer of more importance on the basis of the state of each layer of a retina obtained through an analysis of a cross-sectional image of the retina, the layers are displayed in such a way as to put the focus upon the observation of an important layer, which is advantageous.

Third Embodiment

In the above-described embodiments, an example in which display control of the layers is automatically performed on the basis of the degrees of importance has been described. In this embodiment, a case in which display is controlled by an input made by the operator will be described.

The configuration of an image processing apparatus 11 according to this embodiment is the same as that according to the second embodiment, and therefore description thereof is omitted.

Next, a specific procedure of processing executed in this embodiment will be described with reference to the flowchart of FIG. 6. It is to be noted that steps other than a process for creating a list of layers in step S635 are the same as those in the second embodiment, and therefore description thereof is omitted. A process performed in step S635 in this embodiment will be described hereinafter.

Step S635

In step S635, the list creating unit 150 creates a list of information regarding layers extracted from a cross-sectional image by the analysis unit 130. First, the list of layers is created sequentially from a layer closer to a vitreous body in the anatomical structure. At this time, layers that have not been extracted are deleted from the list. Next, the order of layers in the list is rearranged. Here, the order of the layers is rearranged in the order of the degree of importance of each layer calculated in step S230 by the analysis unit 130. At this time, the most important layer comes at the top of the list. Layers of the same degree of importance are arranged in the order of the anatomical structure.

Next, the list of layers created by the list creating unit 150 is transmitted to the display control unit 140 as information regarding the order of display of a plurality of layers. The display control unit 140 presents the list of layers to the operator, who is not illustrated, using the display apparatus 30. FIG. 7A illustrates an example in which the list of layers illustrated in Table 2 is displayed on the display apparatus 30. There are toggle buttons for selecting layers beside the displayed names of the layers. Layers that the operator wishes to display can be selected by clicking the toggle buttons beside the names thereof. The instruction obtaining unit 120 obtains an instruction input by the operator and transmits the instruction to the list creating unit 150. The list creating unit 150 updates the list of layers on the basis of the instruction for selecting the layers. Furthermore, on the basis of the updated list, the display control unit 140 updates the display of the display apparatus 30. FIG. 7B illustrates an example of display of a state in which the operator has selected the RPE, the GCL, and the IPL.

The order or the priority of the layers in the list of layers may be changed on the basis of an instruction input by the operator. For example, as illustrated in FIG. 7C, the instruction obtaining unit 120 obtains the order of display of the selected layers or the values of importance of the layers as text input.

According to the above-described configuration, by presenting the names of the layers to the operator on the basis of the degrees of importance and by creating the list of layers on the basis of an instruction input by the operator, the operator can easily select layers and put more focus upon observation of the selected layers and recognition of the states of the selected layers.

Fourth Embodiment

In the above-described embodiments, an example in which the order of display and the display time are controlled has been described. In this embodiment, the display control unit 140 controls the method for displaying layers selected for display, in order to provide the optimum method for displaying (presenting) the layers.

The configuration of an image processing apparatus 11 according to this embodiment is the same as that according to the second embodiment, and therefore description thereof is omitted.

Figure 8:
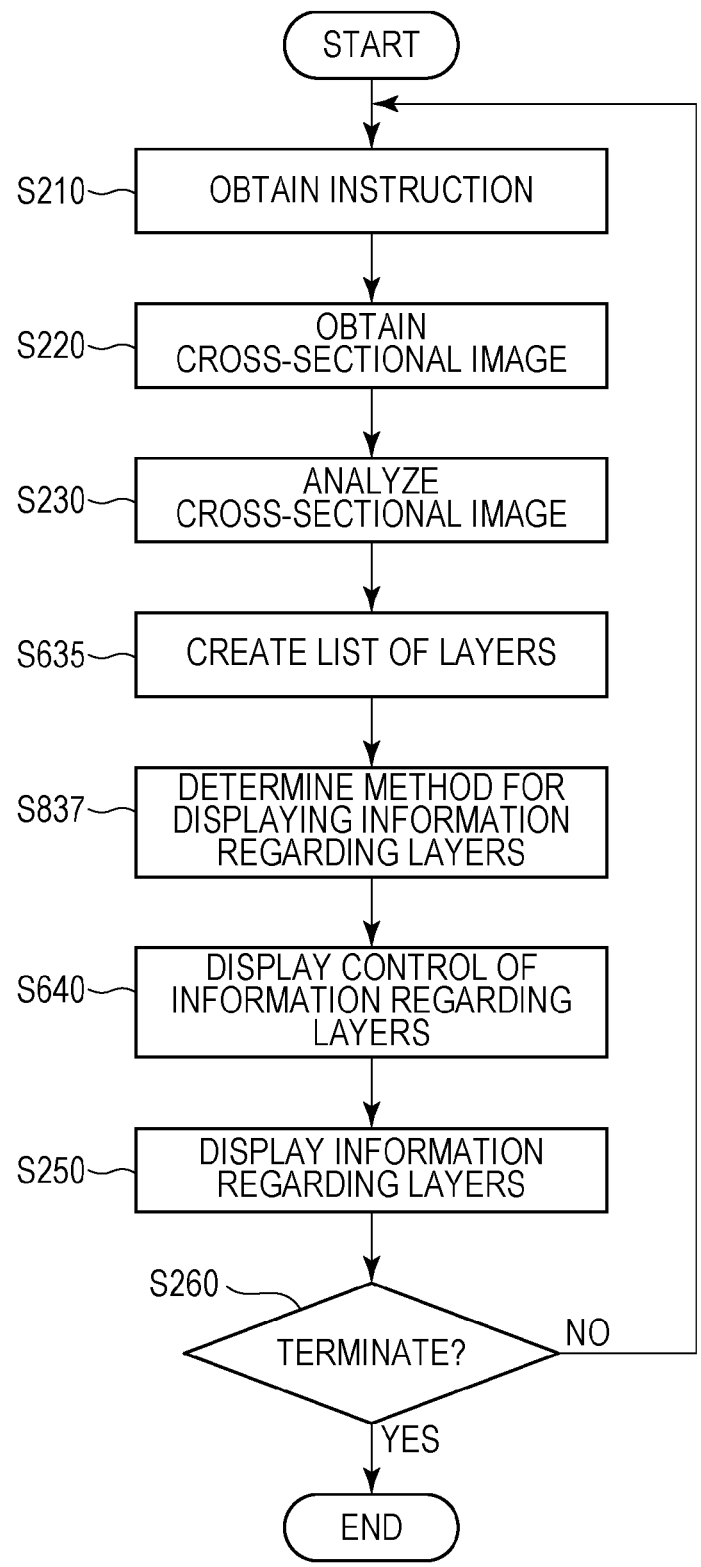
FIG. 8 is a flowchart illustrating a procedure of processing executed by an image processing apparatus 11 according to a fourth embodiment.

Next, a specific procedure of processing executed in this embodiment will be described with reference to a flowchart of FIG. 8. It is to be noted that steps other than a method for displaying the layers in step S837 are the same as those in the third embodiment, and therefore description thereof is omitted.

Step S837

In step S837, the display control unit 140 determines a method for displaying selected layers of a retina. In this embodiment, the display method may be gray-scale display, false-color display, or maximum intensity projection (MIP) display.

Whether layers selected by the display control unit 140 is subjected to gray-scale display, false-color display, or MIP display is selected on the basis of the distribution of pixels of each layer extracted from a cross-sectional image. The layers are then displayed on the display apparatus 30 using the selected display method. The display method is selected under the following conditions.

(1) If the layers to be displayed are layers having low luminance (the GCL, the IPL, the INL, the OPL, and/or the ONL) and if these layers have abnormalities that would be displayed as images having high luminance, MIP display is selected.

(2) If the images of the layers to be displayed have a dynamic range of 256 levels or smaller and the condition (1) is not satisfied, gray-scale display is selected. Here, the distribution of the values of pixels of the layers to be displayed is analyzed and contrast adjustment is performed within the range of contrast that can be realized by the display apparatus 30. Layers having small dynamic ranges include, for example, the GCL, the IPL and the INL.

(3) If both the conditions (1) and (2) are not satisfied, false-color display is selected. If the dynamic range to be used has more than 256 levels and the contrast cannot be realized by the display apparatus 30, the values of luminance are mapped in false color in order to emphasize the distinction between adjacent layers.

It is to be understood that although a dynamic range is considered to be small when the dynamic range has 256 levels or smaller in the above description, the number of levels is not limited to this in this embodiment. Other numbers of levels based on the number of levels that can be realized by a display apparatus may be used.

It is to be understood that the method for determining the display method is not limited to one based on the above-described conditions. For example, the same layer may be sequentially displayed simply using different display methods. Otherwise, the instruction obtaining unit 120 may obtain an instruction input by the operator and a display method selected by the operator may be used to display layers.

According to the above-described configuration, by selecting a display method on the basis of the results of an analysis of layers to be displayed (selected layers), it is possible to put more focus upon observation of a cross-sectional image and recognition of the state of the cross-sectional image. In addition, it is easy to understand information regarding layers extracted from a cross-sectional image.

Other Embodiments

The configurations according to the above-described embodiments of the present invention may be achieved by supplying, to a system or an apparatus, a recording medium on which a program code of software that realizes the functions according to the above-described embodiments has been recoded and by executing the program code stored in the recording medium with an arithmetical unit of the system or the apparatus.

In this case, the program code read from the recording medium realizes the functions according to the above-described embodiments, and the recording medium on which the program code has been recorded configures part of the present invention.

In addition, a case is also included in which the program code read by the computer is executed in order to cause an operating system (OS) operating on a computer to execute part or all of actual processing and the functions according to the above-described embodiments are realized by the processing.

Furthermore, a case is also included in which the program code read from the recording medium is written to a memory in a function enhancing card or a function enhancing unit attached to the computer in order to cause an arithmetical unit in the function enhancing card or the function enhancing unit to execute part or all of actual processing and accordingly the functions according to the above-described embodiments are realized.

If the present invention is applied to the recording medium, a program code corresponding to the diagrams described above is stored in the recording medium.

It is to be understood that the above description of the embodiments is an example of a control unit of an ocular fundus cross-sectional image pickup apparatus according to the present invention, and the present invention is not limited to this.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-192386 filed Aug. 30, 2010, which is hereby incorporated by reference herein in its entirety.

What is claimed is:

1. An image processing apparatus comprising:
  an extraction unit configured to extract a plurality of layers from a cross-sectional image of a retina of an eye;
  an analysis unit configured to obtain information regarding an order of display of the plurality of layers from the cross-sectional image; and
  a display control unit configured to perform control such that the plurality of layers are sequentially displayed on a display unit on the basis of the information regarding the order of display, the plurality of layers being displayed in a display form which is sequentially changed,
  wherein the order of display is determined based on distances from a vitreous body to each of the plurality of layers.

2. The image processing apparatus according to claim 1,
  wherein the display control unit displays, in a two-dimensional manner, the plurality of layers obtained from the cross-sectional image, and
  wherein either boundary lines between the plurality of layers or the plurality of layers themselves are subjected to emphasized display in accordance with the information regarding the order of display.

3. The image processing apparatus according to claim 1,
  wherein the display control unit displays, in a three-dimensional manner, the plurality of layers obtained from the cross-sectional image, and
  wherein either boundary lines between the plurality of layers or the plurality of layers themselves are subjected to emphasized display in accordance with the information regarding the order of display.

4. The image processing apparatus according to claim 1,
  wherein, when displaying the plurality of layers obtained from the cross-sectional image, the display control unit displays a certain layer using a method different from one used to display other layers in accordance with the information regarding the order of display.

5. The image processing apparatus according to claim 1,
  wherein the display control unit sequentially displays only certain layers in accordance with the information regarding the order of display.

6. The image processing apparatus according to claim 1,
  wherein the analysis unit obtains a degree of importance for each of the plurality of layers, and
  wherein the display control unit controls display time of each of the plurality of layers on the basis of the degree of importance.

7. The image processing apparatus according to claim 1, further comprising:
  a list creating unit configured to create a list of the plurality of layers on the basis of the information regarding the order of display,
  wherein the display control unit controls methods for displaying selected layers on the basis of the created list.

8. The image processing apparatus according to claim 7, further comprising:
  an instruction obtaining unit configured to obtain an instruction input from an operator,
  wherein the instruction obtaining unit obtains, from the operator, an instruction regarding an order or display time of the selected layers, and
  wherein the list creating unit creates the list of the plurality of layers on the basis of the obtained instruction.

9. The image processing apparatus according to claim 1,
  wherein the display control unit controls the methods for displaying the plurality of layers in accordance with the information regarding the order of display on the basis of luminance distribution of the plurality of layers.

10. The image processing apparatus according to claim 1, wherein the display control unit displays the plurality of layers using any of the following display methods: grayscale display, false-color display, or maximum intensity projection display.

11. An image processing method comprising the steps of:
extracting a plurality of layers from a cross-sectional image of a retina of an eye;
obtaining information regarding an order of display of the plurality of layers from the cross-sectional image; and
performing control such that the plurality of layers are sequentially displayed on a display unit on the basis of the information regarding the order of display, the plurality of layers being displayed in a display form which is sequentially changed,
wherein the order of display is determined based on distances from a vitreous body to each of the plurality of layers.

12. A non-transitory recording medium comprising:
a program configured to cause a computer to realize the image processing method according to claim 11.

13. An image processing method comprising:
extracting a plurality of layers from a cross-sectional image of a retina of an eye, wherein the layers of the plurality of layers are defined based on distances from a vitreous body;
using a first order-calculation method to generate a first order of display of the plurality of layers from the cross-sectional image;
using a second order-calculation method to generate a second order of display of the plurality of layers from the cross-sectional image;
controlling a display unit to display the plurality of layers in the first order of display; and
controlling the display unit to display the plurality of layers in the second order of display.

* * * * *